United States Patent
Habu et al.

(10) Patent No.: US 7,834,521 B2
(45) Date of Patent: Nov. 16, 2010

(54) ARRAY TYPE ULTRASOUND PROBE, MANUFACTURING METHOD AND DRIVING METHOD OF ARRAY TYPE ULTRASOUND PROBE

(75) Inventors: Takeshi Habu, Hachioji (JP); Takayuki Sasaki, Hachioji (JP); Toshihisa Takeyama, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 815 days.

(21) Appl. No.: 11/811,065

(22) Filed: Jun. 8, 2007

(65) Prior Publication Data

US 2008/0103395 A1    May 1, 2008

(30) Foreign Application Priority Data

Jun. 13, 2006    (JP) ............... 2006-163227

(51) Int. Cl.
*H01L 41/083* (2006.01)
*A61B 8/00* (2006.01)
*G01S 15/00* (2006.01)
*B06B 1/06* (2006.01)

(52) U.S. Cl. ...................... 310/334; 310/322
(58) Field of Classification Search ............. 310/322, 310/334

See application file for complete search history.

(56) References Cited

U.S. PATENT DOCUMENTS

| | | | | |
|---|---|---|---|---|
| 5,142,187 A * | 8/1992 | Saito et al. | ........... | 310/358 |
| 5,381,067 A * | 1/1995 | Greenstein et al. | ........... | 310/334 |
| 5,389,848 A * | 2/1995 | Trzaskos | ........... | 310/322 |
| 6,443,900 B2 * | 9/2002 | Adachi et al. | ........... | 600/458 |
| 2006/0079785 A1 * | 4/2006 | Hosono et al. | ........... | 600/459 |
| 2008/0034873 A1 * | 2/2008 | Habu et al. | ........... | 73/632 |
| 2010/0043190 A1 * | 2/2010 | Habu et al. | ........... | 29/25.35 |
| 2010/0066207 A1 * | 3/2010 | Saito | ........... | 310/335 |

FOREIGN PATENT DOCUMENTS

| | | | |
|---|---|---|---|
| JP | 63-252140 A | | 10/1988 |
| JP | 08-187245 A | | 7/1996 |
| JP | 11-276478 A | | 10/1999 |
| JP | 2001-258879 A | * | 9/2001 |

* cited by examiner

*Primary Examiner*—Thomas M Dougherty
(74) *Attorney, Agent, or Firm*—Holtz, Holtz, Goodman & Chick, P.C.

(57) ABSTRACT

An multi-channel array type ultrasound probe (search unit) disposed at least one-dimensionally, having: a plurality of sheet-shaped piezoelectric elements as transmission reception separation type complex piezoelectric element, wherein a material configuring a transmission piezoelectric element of the complex type piezoelectric element has an elastic coefficient of 10 Gpa to 100 Gpa at 23° C., and a material configuring a reception piezoelectric element of the complex type piezoelectric element has an elastic coefficient of 10 Gpa to 1 Gpa at 23° C.

13 Claims, 4 Drawing Sheets

FIG. 1 ( a ) 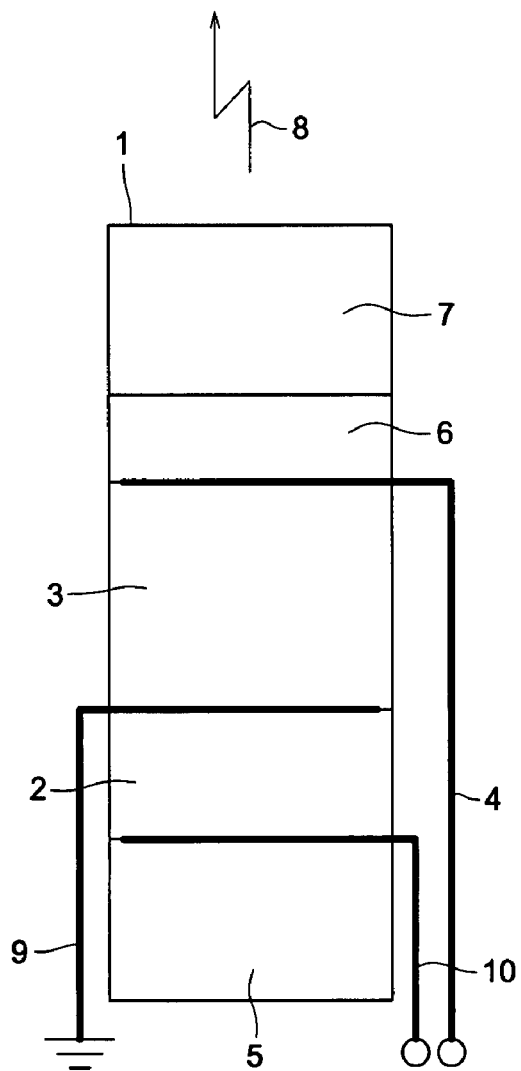
FIG. 1 ( b ) 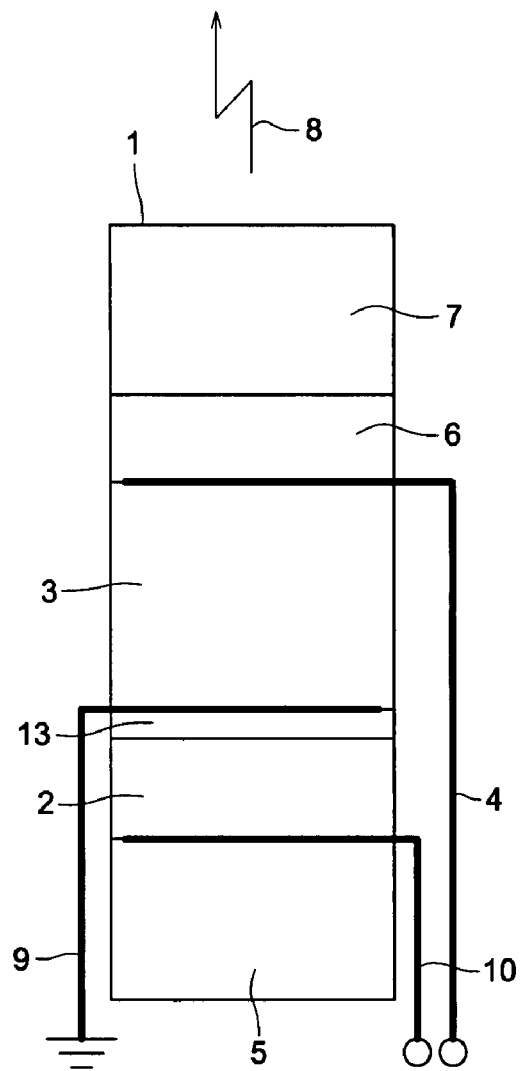

FIG. 3 (a)
FIG. 3 (b)
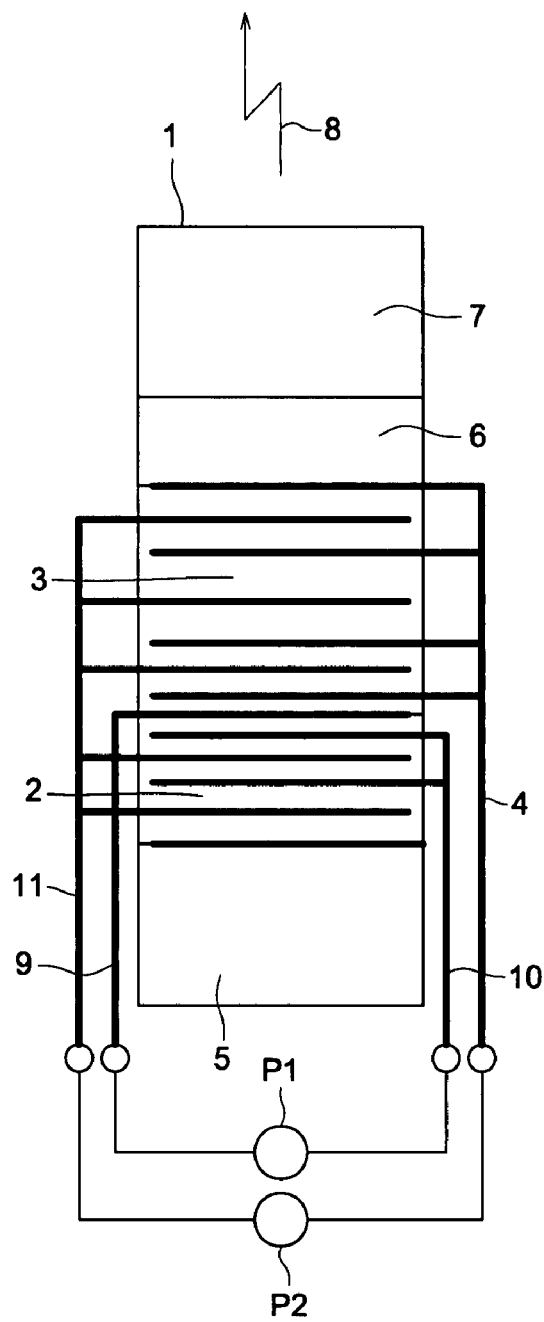
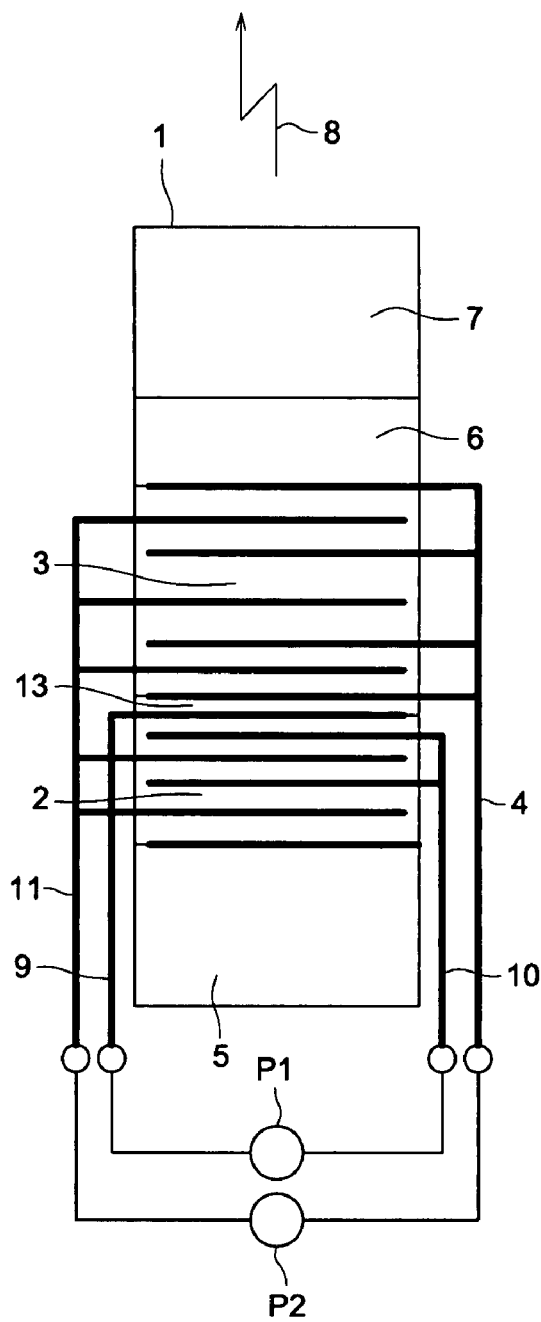

ARRAY TYPE ULTRASOUND PROBE, MANUFACTURING METHOD AND DRIVING METHOD OF ARRAY TYPE ULTRASOUND PROBE

This application is based on Japanese Patent Application No. 2006-163227 filed on Jun. 13, 2006, in Japanese Patent Office, the entire content of which is hereby incorporated by reference.

BACKGROUND OF THE INVENTION

The present invention relates to an array type ultrasound type probe and a manufacturing method and a driving method of the array type ultrasound probe used for medical diagnosis.

An ultrasound diagnosis apparatus is a medical imaging apparatus which obtains a tomography image of a soft tissue of a biological object through ultrasound pulse reflection method without damages. The ultrasound diagnosis apparatus is compact, inexpensive and safety without causing irradiation by X-ray, compared to other medical imaging apparatuses. It is widely used in departments of cardiovascular disease (arteria coronaria of the heart), digestive organs (gastrointestinal), internal medicine (liver, spleen and pancreas), urology (kidney and bladder) and obstetrics and gynecology. Such ultrasound probe used for the ultrasound medical diagnosis apparatus generally utilizes a piezoelectric effect of a piezoceramic so as to perform transmission and reception of ultrasound with a high sensitivity and a high resolution. In this case, as a vibration mode of the piezoelectric element for transmission and reception, a single type prove and an array type probe in which a plurality of probes are disposed two-dimensionally are popularly used. Since array type can obtain a fin image, it is popularly used for the medical image for diagnostic examination On the other hand, since harmonic imaging diagnosis using a harmonic signal can obtain a clear image which conventional B mode diagnosis cannot obtain, it is becoming a standard diagnosis modality. A harmonic imaging technology is a technology to improve a resolution of a ultrasound image and to form a fine image, where the ultrasound probe transmits a fundamental wave (f1) having a certain frequency to an organic object and receives a harmonic wave reflected by the organic object having frequency components, which are integral multiplication (for example, 2 times, 3 times, 4 times and 5 times) of frequency of the aforesaid fundamental wave, and various image processing are carried out after the ultrasound diagnosis apparatus converts the reflected wave into an electric signal. This harmonic imaging technology is also utilized to extract a diagnosis region as an image where a contrast is emphasized by dosing an ultrasound imaging agent including micro bubbles through an artery. The reason is that the micro bubbles dosed into the organic object has a characteristic to reflect the harmonic wave strongly.

It is necessary to improve the image quality of the ultrasound image of the diagnosis region using the harmonic imaging technology also for the ultrasound diagnosis apparatus using an ultrasound probe in which the vibration elements are disposed two-dimensionally. For this purpose, the ultrasound probe in which the vibration elements are arranged two-dimensionally is required to have a frequency characteristic of broad band including frequency components of the fundamental wave and the harmonic wave.

The harmonic imaging has various advantages where a contrast resolution is improved because of a superior S/N ratio due to a small side lobe level, a horizontal resolution is improved since a beam width is thin due to a high frequency, multi reflection does not occur because a fluctuation of a acoustic pressure is small due to a small acoustic pressure at close range, and a diagnosis range can be deeper compared to an ultrasound where a decay beyond a focus is a similar level as the fundamental wave and the fundamental wave has a frequency of the harmonic wave.

As a substantial structure of the array type ultrasound probe for the harmonic imaging, an piezoelectric vibration element where each vibration element configuring an array is a broad band integrated type. There is generally used a method where the fundamental wave is transmitted in a frequency area of a low frequency side of the broad frequency band characteristic and the harmonic wave is received in a high frequency side of the frequency range. Under this circumstances, in conventional ultrasound probes, a technology to improve a sensitivity disclosed in Patent document 1 is know. This technology is to improve the sensitivity. In this technology, the vibration element where microscopic pillar-shaped piezoelectric elements bonded by an organic compound such as, for example, an epoxy resin, is used as an ultrasound transmission-reception element, and each pillar-shaped ceramic is vibrated in longitudinally.

A narrow frequency range ultrasound is used so that a spectrum of the ultrasound for transmitting the fundamental wave and a spectrum of the ultrasound for the receiving harmonic wave do not overlap each other. However, since the narrow frequency range ultrasound is generally an ultrasound pulse signal having a long tail, it negatively affects a resolution in a direction of ultrasound emitting.

As other practical structure of array type ultrasound probe for harmonics imaging, for example, a transmission-reception separation type probe where the transmission piezoelectric vibration element and the reception piezoelectric vibration element are separately disposed is suggested, in Patent document 2 and 3.

For example in Patent document 3, to transmit the fundamental wave and to receive the ultrasound including the harmonic wave, it is suggested that a first piezoelectric layer configured by a plurality of arrayed piezoelectric element having a first acoustic impedance to carry out transmission and reception of the ultrasound having a center frequency of f1, and a second piezoelectric layer configured by a plurality of arrayed second piezoelectric elements having a second acoustic impedance and laid on the first piezoelectric layer to carry out reception of the ultrasound having a center frequency of f2=2×f1 are disposed. However a sufficient sensitivity is not yet obtained.

Further, to improve the sensitivity it is being practiced that a piezoelectric ceramic element is laminated to lower an apparent impedance so that an electrical matching condition with a driving circuit is improved, and an electrical field intensity is increased to create a large distortion so that the transmission sensitivity is improved. However, in an laminated structure, though the remittance sensitivity is increased in accordance with number of the lamination layers, the reception sensitivity is inversely proportional to the number of the lamination layers, thus it is not preferable for the harmonic imaging.

[Patent Document 1] Unexamined Japanese Patent Application Publication No. 63-252140

[Patent Document 1] Unexamined Japanese Patent Application Publication No. 8-187245

[Patent Document 1] Unexamined Japanese Patent Application Publication No. 11-276478

To manufacture the composite piezoelectric vibration element, a piezoelectric ceramic is cut by a cutting machine such as dicer to form a pillar-shaped structure, thereafter a cutting groove is filled with an organic material such as an epoxy resin. Also, in case of the array type probe, separation of each channel is done by the cutting machine such as the dicer.

However, since an transmission-receiving frequency depends on a thickness of the piezoelectric ceramic, the pillar-shaped structure or a channel pitch becomes smaller as the frequency becomes higher. Therefore, there were problems that a mechanical strength of the ceramic is deteriorated in accordance with increase of machine work by cutting machine such as the dicer and a deterioration of properties due to heat and distortion at machining or breakage cannot be ignored, thus a deterioration of an production yield or deterioration of performance of the vibration element or the probe, become easy to be caused. Also, to manufacture the transmission-reception piezoelectric element capable of a desired frequency, it is indispensable to grind and polish both surfaces and is a factor to rise a production cost. As above, there were problems to overcome in the production of the probe using ceramic materials.

SUMMARY OF THE INVENTION

In view of the above problems of the aforesaid conventional art, an object of the present invention is to provide a high sensitive array type ultrasound probe using a ceramic material for a transmission piezoelectric element and using a high sensitive organic piezoelectric element material for reception, particularly in case an array type ultrasound probe in which the operations of remitting and receiving the ultrasound are separated is utilize.

To solve the above problems, in the array type ultrasound probe of the present invention, the transmission and reception piezoelectric element having the laminate structure where the sheet-shaped piezoelectric ceramic configuring each channel are laminated in the single layer or the multi layers, and the sheet shaped piezoelectric element for reception are laminated in a single layer or multi layers to separate transmission and reception for respective piezoelectric elements, and at the same time, the piezoelectric element configured by the ceramic material and the organic material is combined to make the probe a transmission reception separate type. Thus the high sensitive ultrasound prove can be obtained. Further, an organic bonding material is used for combining and an organic bonding layer is brought, thereby the sensitivity is improved further.

Therefore, the present invention can be achieved by the following structures and methods.

(1) A multi-channel array type ultrasound probe disposed at least one-dimensionally, having: a plurality of sheet-shaped piezoelectric elements as transmission-reception separation type complex piezoelectric, wherein a material configuring a transmission piezoelectric element of the complex type piezoelectric element has an elastic coefficient of 10 Gpa to 100 GPa at 23° C., and a material configuring a reception piezoelectric element of the complex type piezoelectric element has an elastic coefficient of 10 Gpa to 1 Gpa at 23° C.

(2) A manufacturing method of the array type ultrasound probe, wherein the reception piezoelectric element of (1) is formed through evaporation polymerizing where a monomer species is formed into a thin film at low temperature on a supporting substance (substrate) selected from polyester resin, polycarbonate resin, and cycloolefin polymer resin.

(3) A driving method of an array type ultrasound probe, wherein transmission and reception are carried out by changing a voltage load alternatively on the transmission piezoelectric element and the reception piezoelectric element.

BRIEF DESCRIPTION OF THE DRAWINGS

FIG. 1(a) is a cross-sectional view of an ultrasound prove.
FIG. 1(b) is a cross-sectional view of an ultrasound prove having an organic bonding layer.
FIG. 3(a) a cross-sectional view of an ultrasound prove where TPE and RPE are laminate layer type.
FIG. 3(b) a cross-sectional view of an ultrasound prove where TPE and RPE are laminate layer type having an organic bonding layer.

DETAILED DESCRIPTION OF THE PREFERRED EMBODIMENT

Figure 2:
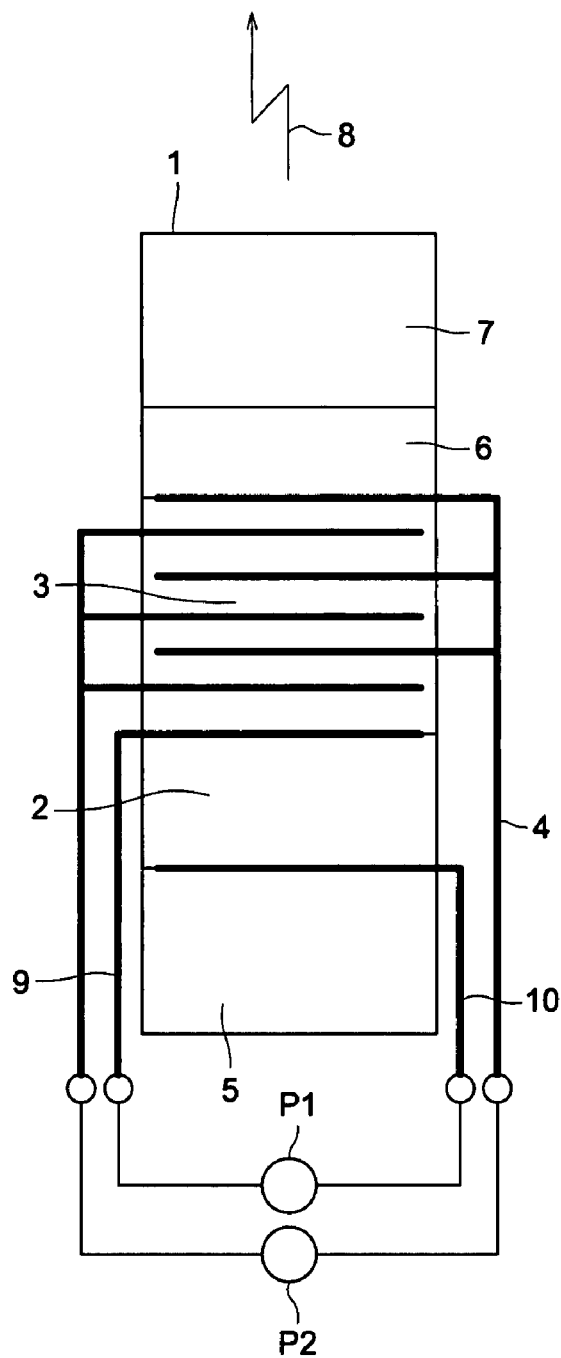
FIG. 2(a) is a cross-sectional view of an ultrasound prove where a reception piezoelectric element is a laminate layer type.
FIG. 2(b) is a cross-sectional view of an ultrasound probe having an organic bonding layer.
Figure 2:
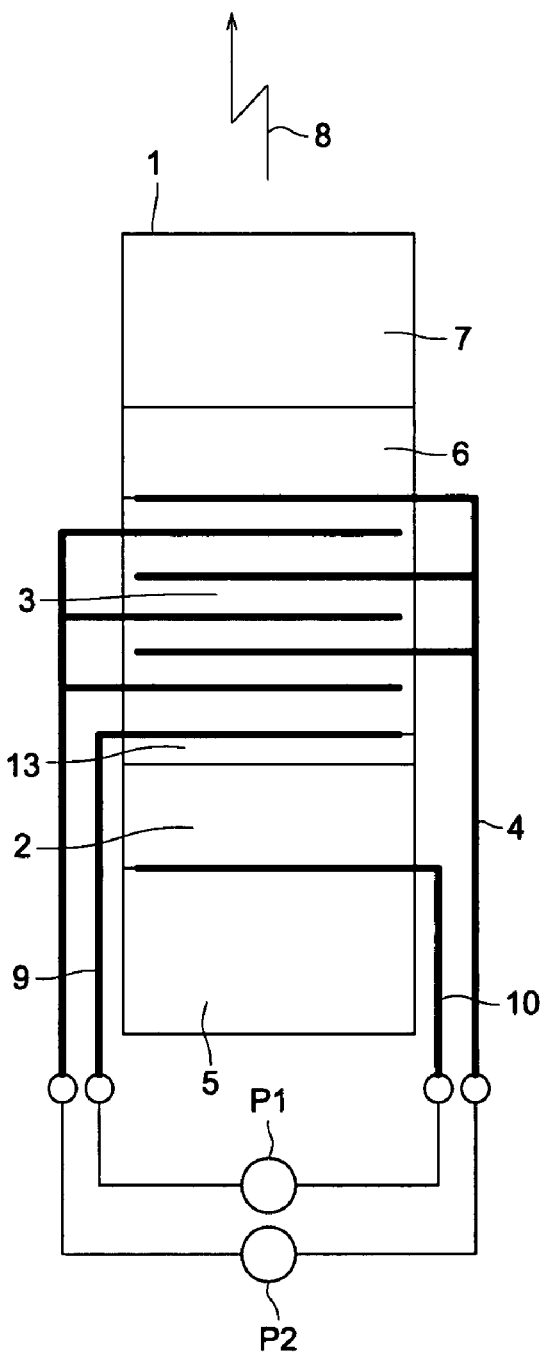
Figure 4:
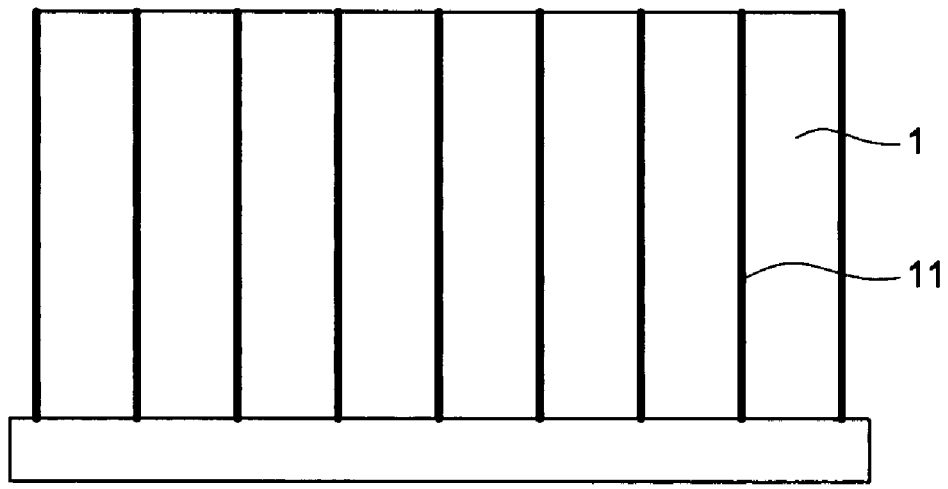
FIG. 4(a) is a side view where probes are arrange parallel in one dimension.
FIG. 4(b) is a side view where probes are arrange parallel in two dimensions.
Figure 4:
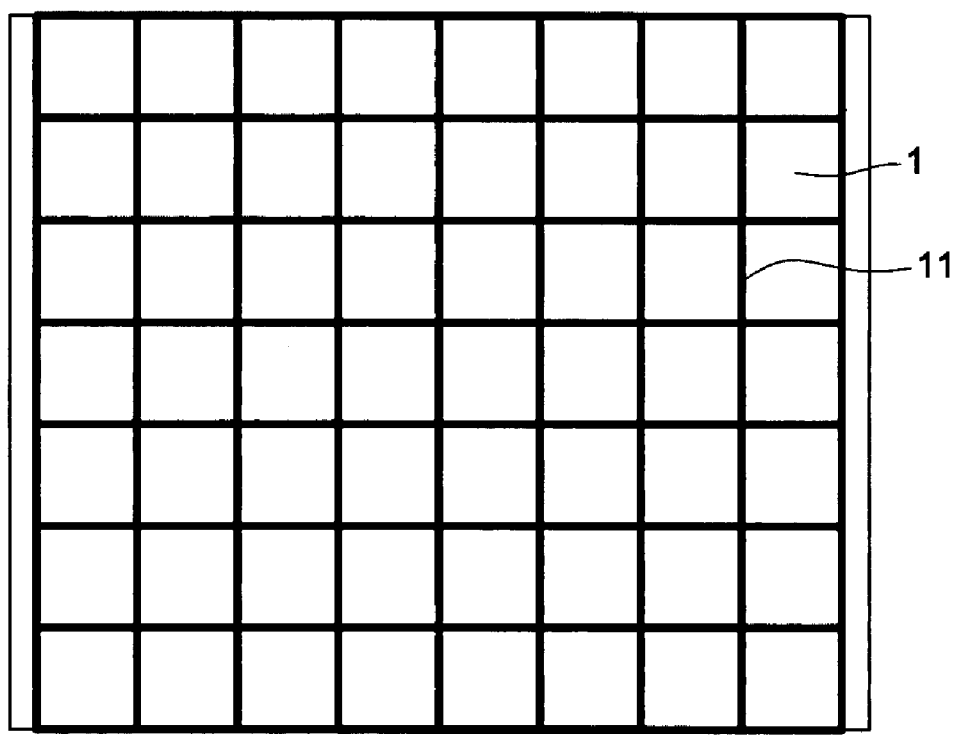

The following is a description of the preferred embodiments of this invention without the present invention being restricted thereto:

The embodiments of this invention are described with reference to FIG. 1 to FIG. 4 as follows.

FIG. 1(a) is a side view of an array type ultrasound probe related to the embodiment of the present invention. FIG. 1(b) is a side view of an ultrasound probe having organic bonding material layer 13. Also, FIG. 2(a) is a cross-sectional view of a lamination layer type transmission piezoelectric element configuring the array type ultrasound probe of the present embodiment. FIG. 2(b) is a side view of an ultrasound probe having organic bonding material layer 13. FIG. 3(a) is a cross-sectional view of an ultrasound prove in which the transmission piezoelectric element and the reception piezoelectric element configuring the array type ultrasound probe related to the embodiment of the present invention are a laminated layer type. FIG. 3(b) is a side view of the ultrasound probe having organic bonding material layer 13. Also, in FIG. 1(a), FIG. 1(b), FIG. 2(a) and FIG. 2(b), numeral 1 represents the ultrasound probe, numeral 2 represents the transmission piezoelectric element, numeral 3 represents the reception piezoelectric element, numeral 4 represents an external electrode to apply voltage to the transmission piezoelectric element, numeral 5 represents a backing member, numeral 6 represents a first aligning layer, numeral 8 indicates an emitting direction of the ultrasound, numeral 9 represents a voltage apply electrode for reception and numeral 13 represents the organic bonding material layer. FIG. 1(a) and FIG. 2(a) are figures in which the bonding materials are not used and FIG. 1(b) and FIG. 2(b) are figures showing examples using the bonding material where a bonding material layer is created between the electrode and the organic piezoelectric element when the organic piezoelectric layer is bonded with the ceramic piezoelectric element through the electrode. In case the ultrasound probe is configured with a single organic piezoelectric element, one organic bonding material layer (unillustrated) can be imposed between an electrode bonded with the ceramic material and the other electrode on opposite side. In case of the laminated layer type (unillustrated) configured by a plurality of the organic piezoelectric elements, the bonding material layer can be disposed for each electrode. It is essential to provide the bonding material layer because a portion where the ceramic piezoelectric element for transmission and the organic piezoelectric element are bonded through the electrode is directly affected by a voltage effect of transmission. FIG. 4(a) is a side view where the probes are arrayed one-dimensionally and FIG. 4(b) is a top view where the probes are arrayed two-dimensionally.

An example of a manufacturing method of the allay type ultrasound probe related to the embodiment of the present invention is explained with reference to FIG. 1 as follows. First, the transmission piezoelectric element 2 is produced. As FIG. 1 shows, the transmission reception separation type piezoelectric element has a structure where transmission piezoelectric element 3 and reception piezoelectric element 2 are laminated. Transmission piezoelectric element 3 can be a structure where thin electrode plates and electrode layers are imposed as FIG. 2. Such structure can be produced in a way, for example, that the electrode is formed on a piezoelectric ceramic green sheet by printing a platinum paste, and it is laminated before calcination then calcinated integrally. A thickness of the green sheet can be easily made not more than 100 μm and the thickness of each layer can be set arbitrarily in accordance with existence or nonexistence of the electrode. Reception organic piezoelectric element 3 can be produced in the same manner as transmission piezoelectric element 2 by laminating the organic polymer sheet. In this case, a portion of the reception piezoelectric element can be formed by laminating only the polymer sheet without printing process of the electrode using the platinum paste, and the electrode can be inserted between the lamination layers as FIG. 3 shows.

For the above lamination and inserting the electrode, the organic bonding material may not use. As a convenient method, a general purpose adhesive can be used. In case the transmission ceramic piezoelectric element and the reception organic piezoelectric element are joined, use of the organic bonding material is preferred since a bonding strength of a boundary surface between the electrode imposing the organic piezoelectric element and the organic piezoelectric element is insufficient, and separation is likely to occur. As preferred organic bonding materials, the following are exemplified without restricting the materials thereof.

They are at least one kind of resin selected from PVB, polyolefine, poly cycloolefin, Polyacrylate, polyamide, polyimide, polyester, polysulfone. As an existing chemical substance in Chemical Substance Control Law, (6)-708 (CASNo. 63148-65-2) (Alkyl(C4)acetalpolyvinylalcohol) is quoted a representative example of PVB. As polyamide, there are quoted polyamide 6, polyamide 66, polyamide 610, polyamide 612, polyamide MXD6, polyamide 11, polyamide 12, polyamide 46 and methoxy-ized polyamide (existing chemical substance (7)-383 etc)(polycondensates of polyalkylen (C3)polyamine/polyalkylene(C4)dicarboxylicacid/urea). polyimide is (7)-2211 (CASNo. 611-79-0). As silicone, there are quoted existing chemical substance (7)-476 polyalkyl (C12)siloxane, (7)-474 (polyalkyl(C12)siloxane), (7)-477 (polyalkyl(hydrogen)siloxane), (7)-483 (polyalkyl(C9)alkeny(C4)siloxane), and (7)-485 (Polyalsodiumalkyl(C4)siliconate). As epoxy, there are a polyphenol type, a poly glycidyl amine type, an alcohol type and an ester type. A cycloaliphatic type is particularly preferred and chemical material numbers of 3-2452(3,(4-epoxycyclohexylmethyl(3, 4-epoxy)cyclohexanecalboxylate), 3-3453, 4-47 (2-(3,4-epoxy)cyclohexyl-5,1-spiro-(3,4-epoxy)cyclohexyl-m-dioxane) and 5-1052 (1,3,5-tris-glycidyl-isocyanuricacid) are preferred.

An usage amount of these resins is adequately determined in accordance with a frequency characteristics and a sensitivity required and is from 10 nm to 60 μm and preferably from 20 nm to 30μ in the thickness.

The resin can be dissolved in solvents such as DMSO, DMF and DME and can be melt by heating bulks up to a melting temperature to be used without using the solvents.

A preferable usage of the organic bonding material is that the bonding material can be used for any layer in lamination of the element and a use of bonding the transmission piezoelectric element and the reception piezoelectric element is preferred. For transmission piezoelectric element, in case the electrode is already formed by printing or applying, it is preferred to be used on the reception piezoelectric element where the electrode is not printed.

In the above lamination layer forming process, joining can be conducted integrally by bonding transmission piezoelectric element 3 and reception piezoelectric element 2 together, where the electrode is printed beforehand either on either the transmission piezoelectric element or on the reception piezoelectric element in a state of a ceramic sheet and an organic thin film sheet respectively. In this case, considering a transmission-reception sensitivity characteristic of the piezoelectric element material and an input/output impedance of a reception circuit, a thickness and a material of each lamination layer structure are selected to produce transmission piezoelectric element 3 and reception piezoelectric element 2. Thus, it is preferred that transmission piezoelectric element 3 and reception piezoelectric element 2 can have the adequately selected impedance respectively. Also, it is possible that only transmission piezoelectric element 3 is produced by calcination through the lamination method of the green sheet and covered by reception piezoelectric element 2 afterward. Or a structure where a sheet is applied and dried in advance then extended through uniaxial extension then laminated and processed, and then is bonded to form grooves between the probes. A lamination layer type where the sheet is extended by uniaxial extension in advance so that the voltage effect is maximized and processed by polarization (poling process) then laminated using the organic bonding material is particularly preferred.

As the organic piezoelectric sheet, copolymer of vinylidene fluoride and olefin fluoride which is high molecule piezoelectric film having a low tensile elastic coefficient are particularly preferred. For example, there is a material which can be obtained by increasing a slow cooling speed of heat treatment process (a process to improve crystalline by apply a heat having a temperature between a ferroelectric-paraelectric phase transition point and a melting point) to about 3° C./minute after forming the film. Further by perform annealing for several 10 minutes (20-30 minutes) at a temperature of 100° C., the elastic coefficient can be lowered. Also, Any other methods to lower a tensile elastic coefficient during the production process can be used.

As of a molecular weight of a polymer raw material, in a high molecule material, as the molecular weight increase, an inherent flexibility of high molecule increases and it becomes the piezoelectric film having a lower tensile elastic coefficient then a high sensitive piezoelectric sheet can be obtained. As of P (VDF-TrFE) and/or (VDF-TeFE), using a high molecule piezoelectric substance of which melt flow rate at 230° C. is not more than 0.02 g/minute and preferably not more than 0.01 g/minute, a high molecule piezoelectric film having low tensile elastic coefficient is realized and a high sensitive piezoelectric sheet can be obtained. The aforesaid VDF means vinylidene fluoride, TrFE indicates 3 ethylene fluorides and TeFE indicates tetra fluoro ethylene.

On the other hand, in case 3 ethylene fluorides, perfluoro alkyl vinyl ether (PFA), perfluoro alkoxy ethylene (PAE), and perfluoro hexa ethylene are copolymerized, an electrical-mechanical binding constant (piezoelectric effect) in a thickness direction varies with a copolymerization rate. For example, the copolymerization rate of vinylidene fluoride in copolymerization is preferred to be 60 mol % to 99 mol %, however, it is also depends on usage of the organic bonding material used for laminating the ceramic piezoelectric element and the organic piezoelectric element, thus an appropriate value varies. The most preferable range of the aforesaid copolymerization rate is 85 mol % to 99 mol %. A polymer including 85 mol % to 99 mol % of vinylidene fluoride and 1 mol % to 15 mol % of perfluoro alkyl vinyl ether, perfluoro alkoxy ethylene and perfluoro hexa ethylene is particularly preferred, since it suppresses the fundamental wave of transmission and improves the reception sensitivity of the harmonic wave in a combination of transmission ceramic piezoelectric element and reception organic piezoelectric element. Conventionally, while tetra fluoro ethylene, 3 ethylene fluorides, were deemed to be adequate, however in the composition element of the present invention perfluoro alkyl vinyl ether (PFA), perfluoro alkoxy ethylene (PAE) and perfluoro hexa ethylene are particularly preferred.

To obtain the high molecule piezoelectric film, it is preferred that poling process is continued until polarity inversion is caused. The polarity inversion is caused by applying a poling electric field which is repeatedly inversed. Forming of such a state of polarity inversion distribution thoroughly, depends on a temperature. At a room temperature, several ten thousands times to several hundred thousands times of polarity inversions are required. However, if it is in a high temperature over 80° C., only several times to several ten times of polarity inversions are required. Also, in case of the reception piezoelectric element, for thin film forming of the element, corona processing of 1 mW/cm$^2$ to 1 kW/cm$^2$ under a normal pressure can be performed.

For the harmonic imaging, the reception piezoelectric element is preferred to be an organic piezoelectric element having sensitivity capable of receiving a second-order harmonic wave generated by the fundamental wave or above. To receive the second-order harmonic wave or above, a resonant frequency of the reception piezoelectric element has to be high in respect to a frequency of the fundamental wave of the transmission piezoelectric element. The fundamental wave frequency f1 is generally selected to be 2 Hz to 20 MHz, and a n-th order harmonic wave is preferred to be 1.5 times to 10 times of the fundamental wave frequency. After transmission piezoelectric element 3 and reception piezoelectric element are bonded, as FIG. 1 to FIG. 3 show, exterior electrode 4 for conducting with the interior electrode of transmission piezoelectric element 3 is formed on a sound wave radiation surface of transmission piezoelectric element 3, on its opposite end surface and on a side surface using a platinum paste, silver paste or silver plating, thus transmission electrode 4, ground electrode 9 and reception electrode 10 are formed. Thereafter, polarization process (poling) is implemented, and after a plurality of unillustrated signal wires are connected with the electrode to form the element of the array type probe, first aligning layer 6, second aligning layer 7 and backing material 5 are joined by bonding method, thereafter cutting groove 6 reaching to backing material 5 is formed by a dicer to separate each channel element, thus the ultrasound prove 1 is formed.

PZT (lead zirconate titanate) is used often as the material of the transmission piezoelectric element, however the materials not containing lead is used recently. They are rock crystal, lithium niobate ($LiNbO_3$), niobic acid tantalic acid potassium [$K(Ta, Nb)O_3$], barium titanate ($BaTiO_3$), lithium tantalate ($LiTaO_3$) and strontium titanate ($SrTiO_3$)

An acoustic lens (not described in the FIG. 1 to FIG. 3) for conversion of ultrasound can be joined with second aligning layer 7. Also, here, while the aligning layer has a two layer structure, it can be a multi layer structure, a single layer structure or a structure without layer in accordance with a subject of examination. Number of layers is preferred to be two to three.

A longitudinal elastic coefficient of the piezoelectric element is represented by a constant of proportion between stress and distortion i.e. a compression force and degree of distortion within an elastic deformation area. In the embodiment of the present invention, the transmission piezoelectric element and the reception piezoelectric element are separated, transmission output is increased as the elastic coefficient increases. However, the longitudinal elastic coefficient of the transmission piezoelectric element under 23° C. is to be between 10 Gpa to 100 Gpa, since the transmission wave shape is distorted and a S/N is deteriorated then noises increase. By the same reason, the higher longitudinal elastic coefficient of the reception piezoelectric element is better, however, since the S/N ration is deteriorated, the elastic coefficient of the reception piezoelectric element under 23° C. is to be between 10 MPa to 1 Gpa.

In manufacturing the reception piezoelectric element of the present invention, there are a radical polymerization method where several monomers are copolymerized using starting agent, a photo polymerization method using a photo sensitizer and an evaporation deposition polymerization where a monomer is evaporated in an low presser atmosphere at a low temperature to form a thin film. In the present invention, one of the above polymerization methods can be adequately selected depending on types of the monomers and relative components proportions of the copolymers. As one of embodiments which preferably operate the reception piezoelectric element, in case of poly urethane, an evaporating deposit copolymerization method is preferable to be used. As monomers for poly urethane, a general chemical formula can indicate $H_2N-R-NH_2$ structure. Here, alkyne group, phenylene group, bivalence heterocycle group and heterocycle group whose R can be substituted by an arbitrary substituent group can be included. Poly urethane can be copolymers of urea derivative and other monomers. As preferable poly urethane, aromatic series poly urethane using 4, and 4'-diamino diphenylmethane (MDA), 4,4'-diphenylmethane diisocyanate (MDI) are quatred.

In case the reception piezoelectric element is manufactured, as a supporting member (substrate) where evaporated monomer is deposited, glass, resin and silicon wafer can be used arbitrarily and for low temperature thin film forming polyethylene phthalate, polyethylenenaphthalate, polyester resin, polycarbonate resin, silicon resin, alkylate resin and cycloolefin resin can be adequately selected.

An operation of the ultrasound probe of the present invention is described with reference to FIG. 3. In FIG. 3, a high voltage plus or a burst signal is supplied from P1 to transmission piezoelectric element 3 at time of remitting. In case of a plus echo mode, transmission piezoelectric element 3 remits a plus ultrasound 8 towards an object to be examined in which a resonance vibration of total thickness mode is excited by a drive plus applied to reception piezoelectric element 2. The ultrasound 8 reflected by the object to be examined goes through transmission piezoelectric element 3 and reaches to reception piezoelectric element 2 to be converted into an electric signal, thereafter it is propagated through an electrode cable to a receiving circuit of a main body as an output. As the above, according to the embodiment of the present invention, in the ultrasound probe used for an ultrasound diagnosis apparatus, a high sensitive probe can be realized by configuring the transmission reception separating type high sensitive array probe with the ceramic material and the organic material.

Further, using the aforesaid ultrasound probe, a high sensitive ultrasound medical diagnosis apparatus can be realized while reducing the cost with workability of the organic material.

EXAMPLE

The following describes the present invention with reference to embodiments without the present invention being restricted thereto.

In the present embodiment, a prototype of the probe and test results of performance and durability were indicated.

Example 1

Manufacturing Array Type Ultrasound Probe 1 to 14

<Manufacturing a Reception Piezoelectric Element Film>
(Manufacturing Film M1)

P(VDF-PFA)(composition mole proportion: VDF/perfluoro akyl vinyl ether) film was formed 48 µm in a thickness by flow casting DMF (dimethylformamide) solution. Further crystallization was carried out at 140° C. Then electrodes were formed on both surfaces by metal evaporation deposit. For this film, polarization inversion was repeated at 77° C. by applying 1 Hz alternative voltage (triangle wave) having a peak value of ±940 V.

(Manufacturing Film M2)

P(VDF-PFA)(composition mole proportion: VDF/perfluoro akyl vinyl ether=88/12) film was formed 48 µm in a thickness by flow casting DMF (dimethylformamide) solution. Further crystallization was carried out at 140° C. Then electrodes were formed on both surfaces by metal evaporation deposit. For this film, polarization inversion was repeated at 82° C. by applying 3 Hz alternative voltage (triangle wave) having a peak value of ±920 V.

(Manufacturing Film M3)

P(VDF-PFA)(composition mole proportion: VDF/HFP Hexafluoropropylene=86/12) film was formed 48 µm in thickness by flow casting DMF (dimethylformamide) solution. Further crystallization was carried out at 138° C. Then electrodes were formed on both surfaces by metal evaporation deposit. For this film, polarization inversion was repeated at 86° C. by applying 2 Hz alternative voltage (triangle wave) having a peak value of ±962 V.

(Manufacturing Film M4)

P(VDF-PFA) (composition mole proportion: VDF/HFP (Hexafluoropropylene=86/12) film was solved in DMF (dimethylformamide) solution and carbon nuno tube was further added 3 weight percent then kneaded by a blender and flow casted into a film having a thickness of 48 µm. Then annealing was carried out at 138° C. Thereafter electrodes are formed on both surfaces of it by metal evaporation deposit. For this film, polarization inversion was repeated at 86° C. by applying 2 Hz alternative voltage (triangle wave) having a peak value of ±962 V.

<Manufacturing Transmission Piezoelectric Element>
(Film S1: Titanic Acid Family Piezoelectric Element not Including Lead)

Basic ingredient components of $CaCO_3$, $La_2O_3$, $Bi_2O_3$ and $TiO_2$, and a sub-ingredient component of MnO are prepared. For basic ingredient components, weight was measured so that a final composition becomes $(Ca_{0.97}La_{0.03})Bi_{4.01}Ti_4O_{15}$. Then, by adding pure water, it is mixed in the pure water using a bowl mill in which zirconia medium is contained, for 8 hours and then thoroughly dried, thus a powder mix was obtained. Next, the powder mix obtained was pre-burned for two hours at 800° C. to produce a pre-burning product. Then pure water was added to the product obtained and fine pulverized is carried out in pure water with the bowl mill in which zirconia medium is contained and then dried, thus ingredient powder for piezoelectric ceramic was produced. In fine pulverization, by changing time and conditions of fine pulverization, the piezoelectric ceramic ingredient powder each having particle diameter of 100 nm was obtained. Each piezoelectric ceramic ingredient powder having different particle diameters to which 6 weight percent of pure water was added as a binder, was formed into a plate-shaped interim compact having thickness of 527 µm. Then after the plate-shaped interim compact was vacuum packed, it was formed by a press having a pressure of 235 Mpa. Next, the compact was burned. Then a final sintered compact having a thickness of 520 µm was obtained. Meanwhile, the burning temperature was 110° C. each. An electric field over 1.5×Ec (MV/m) was applied for one minute to carry out the polarization process.

(Film S2: Manufacturing of Piezoelectric Element PZT)

As components of PZT, lead, zirconium and titanium are within the formula of $Pb(Zr_{(1-x)}Ti_x)O_3(0.47 \leq x \leq 1)$ were prepared. Here, PZT having x=02 was prepared. Each oxidative product was measured and pure water was added. Then it was mixed in pure water with a ball mill containing zirconia medium for 8 hours and dried thoroughly. Thus a powder mix is obtained. The powder mix obtained is temporarily formed and temporarily burned for two hours at 800° C. in the air to make an interim sintered object. Next, pure water was added to the interim sintered object and fine pulverization was carried out in the ball mill containing zirconia medium and then dried. Thus piezoelectric ceramic ingredient powder was produced. To each piezoelectric ceramic ingredient powder having different particle diameters 6 weight percent of pure water was added as a binder, is formed into a plate-shaped interim compact having thickness of 526 µm through a press forming. Then after the plate-shaped interim compact is vacuum packed, it is formed by a press having a pressure of 235 Mpa. Next, the compact was burned and a final sintered compact having a thickness of 520 µm was obtained. Meanwhile, the burning temperature is 780° C. each. An electric field over 1.5×Ec (MV/m) is applied for one minute to carry out the polarization process.

After manufacturing the above ceramic material and organic piezoelectric element, an ultrasound probe was manufactured experimentally. Then fundamental frequency f1 having 7.5 MHz was transmitted a relative reception sensitivity of reception harmonic wave f2 having 15 MHz was investigated. To obtain the relative reception sensitivity, a sound intensity measuring system Model 1805 (1 to 50 MHz) manufactured by Sonora Medical System Inc. was used. Also, as a durability test, 100 hours continuous transmission and reception test was carried out on the experimental probe in a room with a temperature of 60° C. Meanwhile, an aligning layer having two layers and a backing layer to be adaptable to a wavelength of the ultrasound were prepared in advance. The results are shown in the table 1.

TABLE 1

| Prove number | Transmission piezoelectric element | | | Reception piezoelectric element | | | Organic bonding mateerial | | f2 reception | | |
|---|---|---|---|---|---|---|---|---|---|---|---|
| | Kind of film | Thickness (μm) | Elastic coefficient | Kind of film | Elastic coefficient | Thickness (μm) | Kind | Thickness (μm) | relative sensitivity | Durability test | Remarks |
| 1 | S2 | 520 | 60 GPa | S2 | 60 GPa | 520 | Non | Non | 10 | 8 | Comp. |
| 2 | S2 | 520 | 60 GPa | S1 | 75 GPa | 520 | Non | Non | 7 | 5 | Comp. |
| 3 | S2 | 520 | 60 GPa | S1 | 75 GPa | 520 | PVB | 1 | 9 | 7 | Comp. |
| 4 | S2 | 520 | 60 GPa | S1 | 75 GPa | 520 | PVB | 1 | 7 | 5 | Comp. |
| 5 | S2 | 520 | 60 GPa | S2 | 60 GPa | 520 | PVB | 2 | 11 | 9 | Comp. |
| 6 | S2 | 520 | 60 GPa | M1 | 280 MPa | 48 | Non | Non | 26 | 16 | Inv. |
| 7 | S2 | 520 | 60 GPa | M1 | 280 MPa | 48 | PVB | 1 | 30 | 30 | Inv. |
| 8 | S2 | 520 | 60 GPa | M1 | 280 MPa | 48 | Polyimide | 1 | 30 | 33 | Inv. |
| 9 | S2 | 520 | 60 GPa | M2 | 280 MPa | 48 | Epoxy | 1 | 32 | 32 | Inv. |
| 10 | S2 | 520 | 60 GPa | M2 | 280 MPa | 48 | Polyimide | 1 | 30 | 30 | Inv. |
| 11 | S2 | 520 | 60 GPa | M3 | 280 MPa | 48 | PET | 2 | 30 | 29 | Inv. |

* The thickness of the ceramic piezoelectric element is adjusted by grinding

Note 1)
Symbols of organic bonding materials
1 PVB: poly vinyl butyral((6)-708),
2 polyimide: (7)-2211,
3 epoxy: (3)-3453
4 polyester: poly ethylene terephthalate(PET),
5 Silicone: (7)-476
6 Polysulfone: Existing chemical substance number (7)-1262,
7 Olefine: polypropylene
8 polyarylate: condensation product of bisphenol and phthalic acid Note 2)
Elastic coefficient indicates longitudinal elastic coefficient as so called "Young's modulus",
Comp.: Comparative example,
Inv.: The present invention Referring to the above table, according to the present invention, there was realized a transmission and reception separation type high sensitive ultrasound probe using a multi-channel array type ultrasound probe in which a plurality of the proves where the reception piezoelectric having a structure in which the sheet-shaped ceramic material element are laminated in single layer or in multi layers and the reception organic piezoelectric element are combined, are arranged at least one-dimensionally. Further, using the bonding material layer between the organic piezoelectric element and the electrode, the durability can be improved.

Embodiment 2

Manufacturing of Polyurethane Piezoelectric Element by Evaporation Polymerization 4,4' diamino diphenylmethane (MDA), 4,4' diphenylmethane di isocyanato (MDI) were selected as the monomer and evaporation polymerization was carried out. MDA was placed on a tray in a vacuum camber of $2 \times 10^3$ Pa and heated at 100° C. then MDI was heated to be a substrate on an upper part of the chamber. On a polyethylene terephthalate resin (PET) having a thickness of 200 nm on which aluminum evaporation was applied in a thickness of 200 nm beforehand, evaporation was carried out so that the thickness becomes 48 μm. MDA/MDI rate obtained was 1.1. The electrode was applied by aluminum evaporation coating, and polarization (poling) was carried out for 10 minutes at an electric field of 120 MV/m under a temperature of 212° C.

Using the polyurethane film produces (referred as M5), an examination was carried out in the same manner as specimen number 6 in embodiment 1. Here, as the reception piezoelectric element, the aforesaid polyurethane piezoelectric element was used (specimen number 15). As polarization process corona discharge was carried out (specimen number 16). The corona process was carried out at 8 W/cm² at normal temperature. Further, the polyimide bonding material was heat-sealed by 1 μm between the electrode and poly urethane (specimen number 17). Further in the same manner as specimen number 17 of embodiment 2, a probe was produced. Here, a poly urethane film was evaporated 6 μm in the thickness and aluminum was evaporated as the electrode, then this procedure was repeated 8 times to form a polyurethane having seven electrodes of total 48 μm in a thickness. After final evaporation of the electrode was completed, polarization process was carried out through lead wires from the electrodes at 120 MV/m under a temperature of 212° C. for 10 minutes (specimen number 18).

The same evaluation as in embodiment 1 was carried out for the aforesaid specimen and the results are shown in table 2.

TABLE 2

| Prove number | Transmission piezoelectric element | | | Reception piezoelectric element | | | Organic bonding mateerial | | f2 reception | | |
|---|---|---|---|---|---|---|---|---|---|---|---|
| | Kind of film | Thickness (μm) | Elastic coefficient | Kind of film | Elastic coefficient | Thickness (μm) | Kind | Thickness (μm) | relative sensitivity | Durability test | Remarks |
| 15 | S2 | 520 | 60 GPa | M5 | 280 MPa | 48 | Non | Non | 27 | 16 | Inv. |
| 16 | S2 | 520 | 60 GPa | M5 | 280 MPa | 48 | Non | Non | 28 | 16 | Inv. |
| 17 | S2 | 520 | 60 GPa | M5 | 280 MPa | 48 | Polyimide | 1 | 33 | 33 | Inv. |
| 18 | S3 | 521 | 61 GPa | M6 | 281 MPa | 48 | Polyimide | 1 | 33 | 33 | Inv. |

* The thickness of the ceramic piezoelectric element is adjusted by grinding
Note 1)
Symbols of organic bonding materials
1 PVB: poly vinyl butyral ((6)-708),
2 polyimide: (7)-2211,
3 epoxy: (3)-3453
4 polyester: poly ethylene terephthalate(PET),
5 Silicone: (7)-476
6 Polysulfone: Existing chemical substance number (7)-1262,
7 Olefine: polypropylene
8 polyarylate: condensation product of bisphenol and phthalic acid
Note 2)
Elastic coefficient indicates longitudinal elastic coefficient as so called "Young's modulus",
Comp.: Comparative example,
Inv.: The present invention Referring to the table 2, the same preferable performance of the ultrasound probe as in case of embodiment 1 was obtained in evaporation polymerization method also.

According to the above embodiments, in the array type ultrasound probe in which the operation of transmission and reception of the ultrasound is separated, the ceramic material is used for transmission piezoelectric element and a high sensitive organic piezoelectric material is used. Thereby a high sensitive array type ultrasound probe can be provided.

What is claimed is:

1. An multi-channel array type ultrasound probe disposed at least one-dimensionally, comprising:
    a complex piezoelectric element, wherein a plurality of sheet-shaped piezoelectric elements for transmission and for reception are disposed separately;
    wherein a material configuring a transmission piezoelectric element of the complex type piezoelectric element has a longitudinal elastic coefficient of 10 Gpa to 100 GPa at 23° C., and a material configuring a reception piezoelectric element of the complex type piezoelectric element has an elastic coefficient of 10 Mpa to 1 Gpa at 23° C.

2. The array type ultrasound probe of claim 1, wherein in the complex type piezoelectric element, a material configuring the transmission piezoelectric element is a ceramic material and a material configuring the reception piezoelectric element is an organic material.

3. The array type ultrasound probe of claim 1, wherein the reception piezoelectric element is an organic piezoelectric element having a sensitivity capable of receiving a second-order harmonic wave of a fundamental wave transmitted from the transmission piezoelectric element or over.

4. The array type ultrasound probe of claim 3, wherein the organic piezoelectric element is bonded by at least one kind of organic bonding material.

5. The array type ultrasound probe of claim 1, wherein the transmission piezoelectric element or reception piezoelectric element are respectively configured by a piezoelectric element where the same kind of a thin film materials are laminated in layers.

6. The array type ultrasound probe of claim 1, wherein the transmission-reception separation type complex piezoelectric element is imposed between an aligning layer and a backing layer, in a way where the transmission piezoelectric element is disposed on an aligning layer side and the reception piezoelectric element is disposed on a backing side.

7. The array type ultrasound probe of claim 1, wherein the material of the transmission piezoelectric element is lead zirconate titanate, rock crystal, lithium niobate ($LiNbO_3$), potassium niobate tantalate [K (Ta, Nb)$O_3$], barium titanate ($BaTiO_3$), lithium tantalate ($LiTaO_3$), or strontium titanate ($SrTiO_3$).

8. The array type ultrasound probe of claim 1, wherein the material of the reception piezoelectric element is a resin including 60% to 100% by mole of at least one kind selected from polyvinylidene fluoride, polyurea, polyamide, polyimide, polyester and polyolefine.

9. The array type ultrasound probe of claim 4, wherein the organic bonding material is at least one kind of resin from poly vinyl butyral, polyolefine, poly cycloolefin, polyacrylate, polyamide, polyimide, polyester, polysulfone, a silicone, or epoxy and its derivatives.

10. The array type ultrasound probe of claim 1, wherein the material of the reception piezoelectric element is a poly (vinylidene fluoride/perfluoro alkyl vinyl ether, perfluoro alkoxy ethylene) copolymer where vinylidene fluoride presentation is 85% to 99% by mole and perfluoro alkyl vinyl ether, or perfluoro alkoxy ethylene is 1% to 15% by mole.

11. A manufacturing method of the array type ultrasound probe, wherein the reception piezoelectric element of claim 1 is formed through evaporation polymerizing where a monomer species is formed into a thin film at low temperature on a supporting substance (substrate) selected from polyester resin, polycarbonate resin, and cycloolefin polymer resin.

12. A manufacturing method of the array type ultrasound probe of claim 11, wherein the monomer species is at least urea or urea derivative.

13. The array type ultrasound probe of claim 1 is processed by a corona discharging process as a polarization processed (poling).

* * * * *